United States Patent [19]
Grundler et al.

[11] Patent Number: 5,140,025
[45] Date of Patent: Aug. 18, 1992

[54] THIENOTRICYLENE FOR THE TREATMENT OF BRONCHIAL DISEASES

[75] Inventors: Gerhard Grundler; Wolf-Rüdiger Ulrich, both of Konstanz; Ulrich Kilian, Reichenau, all of Fed. Rep. of Germany

[73] Assignee: BYK Gulden Lomberg Chemische Fabrik GmbH, Konstanz, Fed. Rep. of Germany

[21] Appl. No.: 499,403

[22] PCT Filed: Dec. 19, 1988

[86] PCT No.: PCT/EP88/01173
§ 371 Date: Jun. 15, 1990
§ 102(e) Date: Jun. 15, 1990

[87] PCT Pub. No.: WO89/05644
PCT Pub. Date: Jun. 29, 1989

[30] Foreign Application Priority Data
Dec. 22, 1987 [CH] Switzerland .................. 4991/87
Jul. 11, 1988 [CH] Switzerland .................. 2648/88

[51] Int. Cl.$^5$ .................. A61K 31/495; C07D 521/00
[52] U.S. Cl. .................. 514/220; 540/495
[58] Field of Search .................. 540/495; 514/220

[56] References Cited
U.S. PATENT DOCUMENTS
4,381,301  4/1983  Rainer .................. 540/495

Primary Examiner—Robert T. Bond
Attorney, Agent, or Firm—Fleit, Jacobson, Cohn, Price, Holman & Stern

[57] ABSTRACT

The invention relates to the use of telenzepine and (+)-telenzepine in the treatment of bronchial diseases. Furthermore, the the invention relates to (+)-telenzepine, a process for its preparation and intermediates for its preparation.

9 Claims, No Drawings

THIENOTRICYLENE FOR THE TREATMENT OF BRONCHIAL DISEASES

FIELD OF USE OF THE INVENTION

The invention relates to the novel use of a dihydrothienobenzodiazepinone for the preparation of medicaments for the treatment of bronchial diseases, the enantiomers of this dihydrothienobenzodiazepinone, processes for their preparation, and their use.

KNOWN TECHNICAL BACKGROUND

From European Patent 0039519 dihydrothienobenzodiazepinones and their use for the treatment of gastric or intestinal diseases are known. Additionally, it is known that dibenzodiazepinones or pyridobenzodiazepinones can occur in two chiral conformations which are mirror images of one another, and the conformer mixtures can be resolved into the optical antipodes in certain cases—depending on the substitution (German Offenlegungsschrift 3,531,682).

DESCRIPTION OF THE INVENTION

It has now been found that a dihydrothienobenzodiazepinone described in European Patent 0039519, namely the compound 4,9-dihydro-3-methyl-4-[(4-methyl-1-piperazinyl)-acetyl]-10H-thieno[3,4-b][1,5]benzodiazepin-10-one (INN: telenzepine), has unexpectedly pronounced bronchospasmolytic properties. Furthermore, a process has been found, by means of which suitably substituted dihydrothienobenzodiazepinones, in particular telenzepine, can be resolved smoothly and in high yields to their optical antipodes.

The invention therefore relates to the use of 4,9-dihydro-3-methyl-4-[(4-methyl-1-piperazinyl)-acetyl]-10H-thieno[3,4-b][1,5]benzodiazepin-10-one and its pharmacologically tolerated salts for the preparation of medicaments for the treatment and prophylaxis of diseases of the bronchi.

The invention furthermore relates to the use of the (+)-enantiomer of telenzepine, that is to say the (+)-4,9-dihydro-3-methyl-4-[(4-methyl-1-piperazinyl)-acetyl]-10H-thieno[3,4-b][1,5]benzodiazepin-10-one and its pharmacologically tolerated salts for the preparation of medicaments for the treatment and prophylaxis of diseases of the bronchi.

The invention also relates to medicaments which contain the compound (+)-4,9-dihydro-3-methyl-4-[(4-methyl-1-piperazinyl)-acetyl]-10H-thieno[3,4-b]-[1,5]-benzodiazepin-10-one and/or its pharmacologically tolerated salts.

Preferred salts in this context are pharmacologically tolerated salts with inorganic and organic acids usually used in the pharmaceutical sector. The salts with fumaric acid (fumarates), tartaric acid (tartrates) or maleic acid (maleates) may be mentioned as examples. The dihydrochloride may be mentioned as preferred acid addition salt.

The medicaments are prepared by processes known per se, the compounds being used as such, or if required, in combination with suitable pharmaceutical auxiliaries and excipients, in the form of tablets, coated tablets, capsules, suppositories, plasters (for example as TTS), emulsions, suspensions, aerosols or solutions. If, in addition to the active ingredient, the novel pharmaceutical formulations contain pharmaceutical excipients, the content of active ingredient in these mixtures is 0.5 to 95%, preferably 15 to 75%, by weight of the total mixture.

From his technical knowledge, the expert is familiar with the suitable auxiliaries and excipients for the desired medicament formulations. In addition to solvents, gel formers, suppository bases, tablet auxiliaries and other excipients for the active ingredient, it is possible to use, for example, antioxidants, dispersants, solubilizers, dyes, and, in particular, permeation promoters and complex formers (for example cyclodextrins).

The medicaments are used in any suitable formulation, provided that it is ensured that adequate levels of active ingredient are produced and maintained. This can be achieved, for example, by oral or parenteral administration in suitable doses. Usually, the pharmaceutical formulation of the active ingredient is in the form of unit doses adapted to the desired administration. A unit dose may be, for example, a tablet, a coated tablet, a capsule, a suppository or a measured volume of a powder, of granules, of a solution, of an emulsion or of a suspension.

For the purposes of the present invention, "unit dose" is understood as meaning a physically determined unit which contains an individual amount of the active constituent in combination with a pharmaceutical excipient, the content of active ingredient in the said unit corresponding to a fraction or multiple of a single therapeutic dose. The single dose preferably contains the active ingredient in an amount which is administered in an application, and which usually corresponds to a whole daily dose or to a half, a third or a quarter of a daily dose. If only a fraction, such as half or a quarter, of the unit dose is required for an individual therapeutic administration, the unit dose is advantageously divisible, for example in the form of a scored tablet.

If they are present in unit doses and are intended for administration to, for example, humans, the pharmaceutical formulations according to the invention can contain about 0.1 to 10 mg, advantageously 0.5 to 5 mg and in particular 1 to 4 mg of active ingredient.

Therapeutic administration of the pharmaceutical formulation may be effected 1 to 4 times a day at fixed or variable times, for example before each meal and/or in the evening. However, it may be necessary to depart from the stated dosages and to do so depending on the type, body weight and age of the individual to be treated, the type and severity of the disease, the type of formulation and the administration of the formulation and the period or interval within which administration takes place. Thus, it may be sufficient in some cases to manage with less than the above-mentioned amount of active ingredient, whereas in other cases the above-mentioned amount of active ingredient must be exceeded. In acute cases, a higher dose is administered at the beginning of the treatment. After the desired effect has been achieved, the dose is reduced.

The necessary optimal dosage and mode of administration of the active ingredients in each case can be determined by an expert on the basis of his special knowledge.

The pharmaceutical formulations consist, as a rule, of the active ingredient and nontoxic, pharmaceutically tolerated excipients, which are used as a component of the mixture or as a diluent, in solid, semisolid or liquid form, or as a coating agent, for example in the form of a capsule, of a tablet coating, of a bag or of another container, for the therapeutically active constituent. An excipient can serve, for example, as a vehicle to ensure absorption of the medicament by the body, as a formulation auxiliary, as a sweetener, as a flavour adjuster, as a colorant or as a preservative.

For example, tablets, coated tablets, hard and soft capsules, for example of gelatine, dispersible powders, granules, aqueous and oily suspensions, emulsions, solutions or syrups can be used orally.

Tablets can contain inert diluents, for example calcium carbonate, calcium phosphate, sodium phosphate or lactose; granulation and dispersing agents, for example corn starch or alginates; binders, for example starch, gelatine or acacia gum; and lubricants, for example aluminium stearate or magnesium stearate, talc or silicone oil. They may additionally be provided with a coating, which may also be such that it causes delayed dissolution and absorption of the medicament in the gastrointestinal tract, so that, for example, better tolerance, protraction or retardation is achieved. Gelatine capsules can contain the medicament mixed with a solid diluent, for example calcium carbonate or kaolin, or an oily diluent, for example olive oil, peanut oil or liquid paraffin.

Aqueous suspensions, which may be prepared shortly before use, can contain suspending agents, for example sodium carboxymethylcellulose, methylcellulose, hydroxypropylcellulose, sodium alginate, polyvinylpyrrolidone, gum tragacanth or acacia gum; dispersants and wetting agents, for example polyoxyethylene stearate, heptadecaethyleneoxycetanol, polyoxyethylene sorbitol monooleate, polyoxyethylene sorbitan monooleate or lecithin; preservatives, for example methyl or propyl hydroxybenzoates; flavourings; sweeteners, for example sucrose, lactose, sodium cyclamate, dextrose or invert sugar syrup.

Oily suspensions can contain, for example, peanut oil, olive oil, sesame oil, coconut oil or liquid paraffin and thickeners, such as, for example, bee's wax, hard paraffin or cetyl alcohol; and furthermore sweeteners, flavourings and antioxidants.

Water-dispersible powders and granules can contain the medicaments in mixtures with dispersants, wetting agents and suspending agents, for example those mentioned above, and with sweeteners, flavourings and colorants.

. Emulsions can contain, for example, olive oil, peanut oil or liquid paraffin in addition to emulsifiers, such as, for example, acacia gum, gum tragacanth, phosphatides, sorbitan monooleate or polyoxyethylene sorbitan monooleate, and sweeteners and flavourings.

The medicaments are administered rectally using suppositories which are prepared with the aid of binders which melt at rectal temperature, for example cocoa butter or polyethylene glycol.

The medicaments are administered parenterally using aqueous suspensions, isotonic salt solutions or other solutions which can be injected under sterile conditions, may be prepared shortly before use and contain dispersants or wetting agents and/or pharmacologically tolerated diluents, for example propylene glycol and butylene glycol.

Oral administration of the medicaments is preferred.

For use as a bronchospasmolytic, administration of the active ingredients by inhalation is also preferred. The active ingredients are administered either directly as a powder or by atomisation of solutions or suspensions which contain the active ingredients. Atomisation can be effected in a conventional manner, for example by means of compressed-air atomisers or ultrasonic atomisers. Administration from spray cans, in particular those having a conventional metering valve (metered aerosols), is particularly advantageous. By means of metered aerosols, it is possible to provide a defined amount of active ingredient per spray stroke. Particularly advantageous here are so-called synchronous inhalers, by means of which the active ingredient can be administered synchronously with inspiration. Suitable synchronous inhalation apparatuses are disclosed in, for example, German Patent 1,945,257, German Patent 1,917,911 and German Offenlegungsschrift 2,055,734.

For inhalation purposes, the active ingredients are preferably used in micronised form, particle sizes of less than 10 μm being advantageous. For administration from spray cans, the active ingredients are dispersed in conventional propellants, preferably with the aid of a dispersant. Suitable propellants are, in particular, mixtures of trichlorofluoromethane (Frigen ®11) and dichlorodifluoromethane (Frigen ®12), and trichlorofluoromethane can be completely or partially replaced with 1,1,2-trichlorotrifluoroethane (Frigen ®113). Suitable dispersants are, in particular, the sorbitan esters usually used for these purposes (Spane ® from Atlas GmbH) and lecithin. The dispersant is dissolved in the sparingly volatile propellant component initially taken in cooled form. The micronised active ingredient is, or the micronised active ingredients are, stirred into the solution. The dispersion is introduced into spray cans. After crimping, the readily volatile propellant component is forced in.

The active ingredient or ingredients can optionally be formulated with one or more of the stated excipients or additives, also in microencapsulated form.

Chronic obstructive respiratory tract diseases of various origins (for example bronchitis, bronchial asthma) in humans or animals, which can be treated with telenzepine or (+)-telenzepine owing to the outstanding bronchospasmolytic properties, may be mentioned as examples of diseases of the bronchi. The invention thus also relates to a method for the treatment of mammals, in particular humans, who have diseases of the bronchi. The method is characterised in that a therapeutically effective and pharmacologically tolerated amount of telenzepine or (+)-telenzepine is administered to the individual suffering from a bronchial disease. Telenzepine is known from European Patent 0039519. The (+)-enantiomer of telenzepine is prepared by a novel process which is also subject of the invention. This process, for which the separation of enantiomers via the diasteromeric salts disclosed in German Offenlegungsschrift 3,531,682 gave no suggestion, is characterised in that telenzepine (=compound of the formula I), as such or in its deprotonated form.

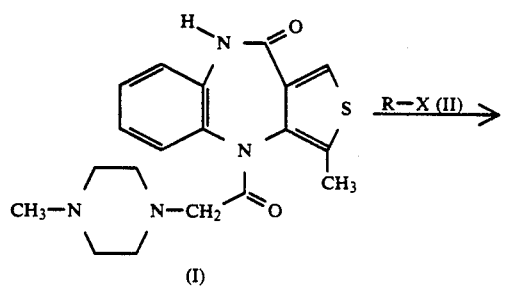

-continued

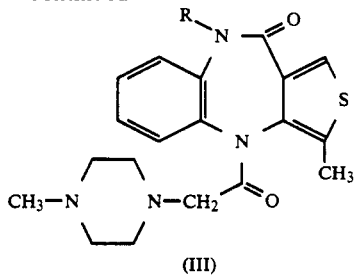

is reacted with a chiral compound which has a uniform configuration and is of the formula II, wherein R represents a chiral radical having a uniform configuration and X represents a leaving group, the diastereomer mixture III obtained is separated, and the compounds I having a uniform conformation are liberated from the optically pure diastereomers.

Suitable compounds of the formula II are in principle all chiral compounds which have a uniform configuration and are capable of reacting with the compound I or its anion with elimination of the leaving group X, and whose radical R can be eliminated again smoothly and without undesirable side reactions, after the separation of the diastereomers. Suitalbe leaving groups X are, in particular, all nucleophilically displaceable atoms or groups, such as, for example, halogen atoms (I, Br or, in particular, Cl) or hydroxyl groups activated by esterification (for example with sulphonic acids) (—O—SO$_2$—CH$_3$, —O—SO$_2$—CF$_3$ or —O—SO$_2$—C$_6$H$_4$—p—CH$_3$).

Suitable radicals R are all radicals which have a uniform configuration and which can be derived from naturally occurring or synthetically obtainable chiral compounds and which can be eliminated solvolytically under mild, preferably slightly acidic conditions from the compounds III. The following may be mentioned in particular as radicals R:

- glycosyl radicals which are derived from glycopyranoses, glycofuranoses or oligosaccharides and which, if desired, are partially or completely protected with protective groups conventionally used in carbohydrate chemistry, or
- chiral terpene alcohol radicals bonded via the oxygen atom, or
- other chiral alcohol radicals bonded via the oxygen atom, each of which carries a carbonyl group or, in particular, a methylene group on the oxygen atom functioning as a linking member.

Preferred radicals R are radicals of the formula IV

R1—O—CH$_2$— (IV)

wherein R1 together with the oxygen atom to which it is bonded represents a glycosyl radical, a chiral terpene alcohol radical or another chiral alcohol radical.

The radicals which are derived from naturally occurring mono- or disaccharides, such as arabinose, fructose, galactose, glucose, lactose, mannose, ribose, xylose, maltose, sorbose or N-acetyl-D-glucosamine, may be mentioned as examples of glycosyl radicals R1—O—.

Radicals which are derived from a naturally occurring or readily synthesizable terpene alcohol may be mentioned in particular as chiral terpene alcohol radicals R1—O—. The following may be mentioned as examples of terpene alcohols: isopulegol, neomenthol, isomenthol, menthol, carveol, dihydrocarveol, terpinen-4-ol, mirtenol, citronellol, isoborneol, borneol, fenchol and, in particular, isopinocampheol.

The radicals which are derived from the following alcohols may be mentioned as examples of other chiral alcohol radicals R1—O—: mandelic esters, cinchonidine, cinchonine, ephedrine, serine methyl ester, sitosterol, methyl 3-hydroxy-2-methylpropionate and ethyl lactate.

A particularly perferred radical R is the isopinocampheyloxymethyl radical.

The reaction of the compound I with the compound II is carried out in a manner known per se. To increase the nucleophilicity of the compound I, it is expedient to deprotonate it. The deprotonating agents used can be the bases conventionally employed for analogous reactions in organic chemistry, for example hydroxides, such as sodium hydroxide or potassium hydroxide, or carbonates, such as potassium carbonate, or alcoholates, such as sodium methylate or sodium ethylate, or amines, such as pyridine, triethylamine or ethyldiisopropylamine or organometallic compounds, such as tert-butyllithium, or preferably hydrides, such as sodium hydride.

Deprotonation of the compound I and subsequent reaction with compound II are carried out in inert protic or aprotic solvents, depending on the deprotonating agent. Examples of suitable solvents are methanol, isopropanol, dimethyl sulphoxide, acetone, acetonitrile, dioxane and preferably dimethylformamide.

The deprotonation of compound I is preferably carried out at temperatures between −30° C. and +100° C., in particular at temperatures between 0° C. and 50° C., depending on the reactivity of the deprotonating agent. The subsequent reaction of the deprotonated compound I with compound II is carried out at temperatures which—in order to avoid undesirable side reactions—should not exceed 50° C. and are preferably between −20° C. and +20° C.

Separation of the diastereomer mixture obtained after the reaction of I with II is effected in a manner known per se, for example by chromatography over suitable columns or preferably by fractional crystallisation. If the separation is to be carried out by crystallisation, it is expedient to convert the resulting diastereomers into suitable, readily crystallising salts. Examples of suitable salts are the oxalate, the tosylate, the fumarate and in particular the maleate.

Liberation of the compounds III from their salts after separation of the diastereomers is carried out with the aid of suitable bases which are not too strong. For example, bicarbonates, such as sodium bicarbonate, are suitable for this purpose.

The compounds I having a single conformation are liberated from the optically pure diastereomers by solvolysis under mild, slightly acidic conditions. For example, anhydrous formic acid with added hydrogen chloride has proved to be a reagent suitable for the solvolysis.

The compounds of the formula II are known or they are obtainable by analogous means from known compounds in a manner familiar to those skilled in the art. Thus, for example, the compounds II in which R has the meaning of formula IV and X represents a chlorine atom can be prepared by chloromethylation of corresponding alcohols [for example in analogy to R. C. Ronald et al., J. Org. Chem. 45 (1980), 2224].

The compounds I which are obtained after a liberation from the optically pure diastereomers, have a single conformation and rotate linearly polarised light of wavelength 589 nm in the (+) or (−) direction, in other words (+)-4,9-dihydro-3-methyl-4-[(4-methyl-1-piperazinyl)-acetyl]-10H-thieno-[3,4-b]-[1,5]benzodiazepin-10-one and (−)-4,9-dihydro-3-methyl-4-[(4-methyl-1-piperazinyl)-acetyl]-10H-thieno-[3,4-b][1,5]benzodiazepin-10-one, and their salts are novel compounds with surprising pharmacological properties.

The invention therefore furthermore relates to (+)-4,9-dihydro-3-methyl-4-[(4-methyl-1-piperazinyl)-acetyl]-10H-thieno-[3,4-b][1,5]benzodiazepin-10-one and its salts.

The invention also relates to (−)-4,9-dihydro-3-methyl-4-[(4-methyl-1-piperazinyl)-acetyl]-10H-thieno-[3,4-b][1,5]benzodiazepin-10-one and its salts. Preferred salts in this connection are pharmacologically tolerated salts with inorganic and organic acids usually used in the pharmaceutical sector. The dihydrochloride may be mentioned as a preferred acid addition salt.

The invention furthermore relates to the compounds of the formula III, wherein R has the above-mentioned meaning, which occur as intermediates in the process according to the invention, and their salts.

The examples which follow illustrate the invention in more detail without restricting it.

EXAMPLES

1.

4,9-Dihydro-9-[(+)-isopinocampheyloxymethyl]-3-methyl-4-[(4-methyl-1-piperazinyl)-acetyl]-10H-thieno[3,4-b][1,5]benzodiazepin-10-one 109.6 g of 4,9-dihydro-3-methyl-4-[(4-methyl-1-piperazinyl)-acetyl]-10H-thieno[3,4-b][1,5]benzodiazepin-10-one are suspended in 2.2 l of anhydrous dimethylformamide under a nitrogen atmosphere and heated to 40°. 14.2 g of sodium hydride (80% strength suspension in liquid paraffin) are added in the course of 2.5 hours, while stirring. Thereafter, the mixture is stirred for 16 hours at room temperature. It is then cooled to +5° C., and 41.6 g of (+)-isopinocampheyl chloromethyl ether are added dropwise in the course of 30 minutes. The mixture is stirred for a further 30 minutes at 5° C., after which 150 ml of glacial acetic acid are added dropwise. The solution is evaporated down in a rotary evaporator. The residue is dissolved in 300 ml of water. The solution is first adjusted to pH 1–2 with 2N HCl. After 5 minutes, solid sodium bicarbonate is added until a pH of 9 is obtained. After extraction with 3×200 ml of ethyl acetate, drying over sodium sulphate and evaporation, 97.0 g of crude product are obtained as a viscous oil. Purification is effected by chromatography over silica gel. (Mobile phase: toluene/dioxane/methanol = 70:15:15). 76.1 g (69%) of the title compound are isolated as a colourless, amorphous solid. ($[\alpha]_D^{22} = +25.2°$); c = 1, dichloromethane/methanol = 1:1).

2.

4,9-Dihydro-9-[(−)-isopinocampheyloxymethyl]-3-methyl-4-[(4-methyl-1-piperzinyl)-acetyl]-10H-thieno[3,4-b][1,5]benzodiazepin-10-one 6.3 g (58%) of the title compound are isolated as a colourless, amorphous solid ($[\alpha]_D^{22} = -23.1°$; c = 1, dichloromethane/methanol = 1:1) by the method stated for Example 1, starting from 10.0 g of 4,9-dihydro-3-methyl-4-[(4-methyl-1-piperazinyl)-acetyl]-10H-thieno[3,4-b][1,5]benzodiazepin-10-one and 4.1 g (−)-isopinocampheyl chloromethyl ether.

3.

(+)-4,9-Dihydro-9-[(+)-isopinocampheyloxymethyl]-3-methyl-4-[(4-methyl-1-piperazinyl)-acetyl]-10H-thieno[3,4-b][1,5]benzodiazepin-10-one maleate 76.0 g of 4,9-dihydro-9-[(+)-isopinocampheyloxymethyl]-3-methyl-4-[(4-methyl-1-piperazinyl)-acetyl]-10H-thieno[3,4-b][1,5]benzodiazepin-10-one and 16.4 g of maleic acid are dissovled in 1.5 l of ethanol while heating (to 70° C.). 19.2 g (20%) of the title compound crystallise out of this solution after 16 hours at room temperature and 1 hour at +10° C. Melting point: 205° C.; ($[\alpha]_D^{22} = +98.2°$, c = 1, dichloromethane/methanol = 1:1).

4.

(−)-4,9-Dihydro-9-[(−)-isopinocampheyloxymethyl]-3-methyl-4-[(4-methyl-1-piperazinyl)-acetyl]-10H-thieno[3,4-b][1,5]benzodiazepin-10-one maleate 5.8 g of 4.9-dihydro-9-[(−)-isopinocampheyloxymethyl]-3-methyl-4-[(4-methyl-1-piperazinyl)-acetyl]-10H-thieno[3,4-b][1,5]benzodiazepin-10-one and 1.25 g of maleic acid are dissolved in 140 ml of ethanol, while heating (70° C.). 2.1 g of a diastereomer mixture (with $[\alpha]_D^{22} = 77°$; c = 1, dichloromethane/methanol = 1:1) crystallise out of this solution after 16 hours at room temperature and 1 hour at 0° C. 1.8 g of this mixture are recrystallised from 30 ml of ethanol. 850 mg (14%) of the title compound are isolated as colourless crystals of melting point 207° C. ($[\alpha]_D^{22} = -96.4°$; c = 1, dichloromethane/methanol = 1:1).

5.

(+)-4,9-Dihydro-9-[(+)-isopinocampheyloxymethyl]-3-methyl-4-[(4-methyl-1-piperazinyl)-acetyl]-10H-thieno[3,4-b][1,5]benzodiazepin-10-one 10.0 g of (+)-4,9-dihydro-9-[(+)-isopinocampheyloxymethyl]-3-methyl-4-[(4-methyl-1-piperazinyl)-acetyl]-10H-thieno[3,4-b][1,5]benzodiazepin-10-one maleate are suspended in 100 ml of water, and 1.4 g of sodium bicarbonate are added. The solution is extracted with 3×100 ml of ethyl acetate; the organic extracts are dried over sodium sulphate and then evaporated down. 8.1 g (99%) of the title compound are isolated as a colourless, amorphous solid. ($[\alpha]_D^{22} = +96.1°$; c = 1, dichloromethane/methanol = 1:1).

6.

(−)-4,9-dihydro-9-[(−)-isopinocampheyloxymethyl]-3-methyl-4-[(4-methyl-1-piperazinyl)-acetyl]-10H-thieno[3,4-b][1,5]benzodiazepin-10-one 700 mg of (−)-4,9-dihydro-9-[(−)-isopinocampheyloxymethyl]-3-methyl-4-[(4-methyl-1-piperazinyl)-acetyl]-10H-thieno[3,4-b][1,5]benzodiazepin-10-one maleate and 200 mg of sodium bicarbonate are reacted by the method described for Example 5. 550 mg (96%) of the title compound are isolated as a colourless, amorphous solid. ($[\alpha]_D^{22} = -96.6°$; c = 1, dichloromethane/methanol = 1:1).

7.

(+)-4,9-dihydro-3-methyl-4-[(4-methyl-1-piperazinyl)-acetyl]-10H-thieno[3,4-b][1,5]benzodiazepin-10-one 6.6 g of (+)-4,9-dihydro-9-[(+)-isopinocampheyloxymethyl]-3-methyl-4-[(4-methyl-1-piperazinyl)-acetyl]-

10H-thieno[3,4-b][1,5]benzodiazepin-10-one are dissolved, at room temperature, in 66 ml of formic acid to which hydrogen chloride has been added (dry hydrogen chloride gas is passed into 100 ml of formic acid at room temperature for 5 minutes). After 5 minutes, the solvent is stripped off in a rotary evaporator and the residue is taken up in 100 ml of water. The solution is adjusted to pH 1-2 with 2N HCl and then extracted with 3×50 ml of dichloromethane. Thereafter, the aqueous phase is adjusted to pH 9 with sodium bicarbonate and extracted with 3×100 ml of dichloromethane. After drying over sodium sulphate, the organic extracts are evaporated down. The residue is purified by chromatography over silica gel (mobile phase: toluene/dioxane/methanol=70:15:15). 3.5 g (67%) of the title compound are isolated as a colourless, amorphous solid. ($[\alpha]_D^{22}$=+41.2°, c=1, dichloromethane/methanol=1:1; $[\alpha]_D^{22}$=+32.4°, c=1, chloroform; the melting point of the dihydrochloride (2 HCl×1.1 H$_2$O) is 223°-229° C. (decomposition); $[\alpha]_D^{22}$=+26.4°, c=1, water). 8. (−)-4,9-dihydro-3-methyl-4-[(4-methyl-1-piperazinyl)-acetyl]-10H-thieno-[3,4-b][1,5]benzodiazepin-10-one 400 mg of (−)-4,9-dihydro-9-[(−)-isopinocampheyloxymethyl]-3-methyl-4-[(4-methyl-1-piperazinyl)-acetyl]-10H-thieno[3,4-b][1,5]benzodiazepin-10-one are reacted in 4 ml of formic acid/HCl and purified, as described for Example 7. 250 m (90%) of the title compound are isolated as a colourless, amorphous solid. ($[\alpha]_D^{22}$=−41.0°, c=1, dichloromethane/methanol=1:1; $[\alpha]_D^{22}$=−32.5°, c=1, chloroform; the melting point of the dihydrochloride (2 HCl×H$_2$O) is 223°-229° C. (decomposition); $[\alpha]_D^{22}$=−26.3°, c=1, water).

INDUSTRIAL APPLICATION

The compounds 4,9-dihydro-3-methyl-4-[(4-methyl-1-piperazinyl)-acetyl]-10H-thieno[3,4-b][1,5]benzodiazepin-10-one and (+)-4,9-dihydro-3-methyl-4-[(4-methyl-1-piperazinyl)-acetyl]-10H-thieno[3,4-b][1,5]benzodiazepin-10-one and their pharmacologically tolerated salts have novel, previously unknown pharmacological properties which make them industrially useful. Thus, these compounds prove to be very valuable for the treatment of bronchial diseases and are therefore outstandingly suitable for use in human and veterinary medicine.

The excellent bronchial-therapeutic properties of the two compounds are displayed in particular in a unique bronchospasmolytic activity. This bronchospasmolytic activity can be observed even when very low doses are administered. Particularly surprising in this connection is the high specificity, the continuous and non-excessive action following intravenous injection and especially the very long-lasting bronchospasmolytic action, which makes the substances appear outstandingly suitable for the therapy of asthmatic diseases, the substances being particularly suitable for therapy of night-time asthma attacks, owing to the unexpected and surprising long duration of action.

With their excellent efficacy, in conjunction with the lack of significant side effects and only a small effect on the cardiovascular system, the compounds (±)-telenzepine and (+)-telenzepine prove to be clearly superior to the bronchospasmolytics known from the prior art. It should be emphasized that (±)-telenzepine and (+)-telenzepine are so far the only compounds with this type of activity shown to be effective after intravenous, intratracheal (i.t.) and oral administration.

Furthermore, the compound (+)-4,9-dihydro-3-methyl-4-[(4-methyl-1-piperazinyl)-acetyl]-10H-thieno[3,4-b][1,5]benzodiazepin-10-one proves to be a highly effective antimuscarinic, which, because of its superior antiulcerogenic properties and inhibiting properties with respect to gastric juice secretion, is outstandingly suitable for use in human and veterinary medicine. Surprisingly, (+)-4,9-dihydro-3-methyl-4-4-[(4-methyl-1-piperazinyl)-acetyl]-10H-thieno[3,4-b][1,5]benzodiazepin-10-one exhibits much more pronounced muscarine-antagonistic properties than (−)-4,9-dihydro-3-methyl-4[(4-methyl-1-piperazinyl)-acetyl]-10H-thieno[3,4-b][1,5]benzodiazepin-10-one, as it has been possible to detect in receptor affinity studies.

The compound (+)-4,9-dihydro-3-methyl-4-[(4-methyl-1-piperazinyl)-acetyl]-10H-thieno[3,4-b][1,5]benzodiazepin-10-one substantially inhibits gastric juice secretion of warm-blooded animals and furthermore has an excellent protective effect with respect to the stomach and intestine in warm-blooded animals. This protective action with respect to the stomach and intestine is even observed with the administration of doses which are below the doses which inhibit acid secretion. Furthermore, the compound (+)-4,9-dihydro-3-methyl-4-[(4-methyl-1-piperazinyl)-acetyl]-10H-thieno[3,4-b][1,5]-benzodiazepin-10-one is distinguished by the lack of significant side effects and a high therapeutic index.

"Stomach and intestine protection" is understood in this context as meaning the prevention and treatment of gastrointestinal diseases, in particular inflammatory gastrointestinal diseases and lesions (such as, for example, ventricular ulcer, duodenal ulcer, gastritis or gastric irritation due to hyperacidity or medicaments), which may be caused, for example, by microorganisms, bacterial toxins, medicaments (for example certain antiinflammatory agents and antirheumatics), chemicals (for example ethanol), gastric acid or stress situations.

With its excellent properties, the compound (+)-4,9-dihydro-3-methyl-4-[(4-methyl-1-piperazinyl)-acetyl]-10H-thieno[3,4-b][1,5]benzodiazepin-10-one surprisingly proves to be superior to the conformer mixture known from the prior art (European Patent 39,519), in other words (±)-4,9-dihydro-3-methyl-4-[(4-methyl-1-piperazinyl)-acetyl]-10H-thieno[3,4-b][1,5]benzodiazepin-10-one. Because of these properties, the (+)-conformer and its pharmacologically tolerated salts are also outstandingly suitable for use in human and veterinary medicine for the treatment and/or prophylaxis of gastrointestinal diseases and diseases which are due to gastric hyperacidity.

The invention therefore also relates to the compound (+)-4,9-dihydro-3-methyl-4-[(4-methyl-1-piperazinyl)-acetyl]-10H-thieno[3,4-b][1,5]-benzodiazepin-10-one for use in the treatment and/or prophylaxis of gastrointestinal diseases and diseases which are due to gastric hyperacidity.

The invention also embraces the use of the compound (+)-4,9-dihydro-3-methyl-4-[(4-methyl-1-piperazinyl)-acetyl]-10H-thieno[3,4-b][1,5-benzodiazepin-10-one for the preparation of medicaments which are used for the treatment and/or prophylaxis of gastrointestinal diseases and diseases which are due to gastric hyperacidity.

If the compound (+)-4,9-dihydro-3-methyl-4-[(4-methyl-1-piperazinyl)-acetyl]-10H-thieno[3,4- b][1,5]benzodiazepin-10-one and/or its salts are to be used for the treatment and/or prophylaxis of gastrointestinal diseases and diseases which are due to gastric hyperacidity, the pharmaceutical formulations can also contain one or more pharmacologically effective constituents of other groups of medicaments, such as antacids, for example aluminium hydroxide or magnesium aluminate; other drugs which inhibit acid secretion, such as, for example, H₂-blockers (for example cimetidine or ranitidine); tranquillizers, such as benzodiazepines, for example diazepam, spasmolytics, such as, for example, bietamiverine or camylofine; anticholinergics, such as, for example, oxyphencyclimine or phencarbamide; local anaesthetics, such as, for example, tetracaine or procaine; possibly also ferments, vitamins or amino acids. The compound (+)-4,9-dihydro-3-methyl-4-[(4-methyl-1-piperazinyl)-acetyl]-10H-thieno[3,4-b][1,5]-benzodiazepin-10-one can also be used for the prevention of gastrointestinal diseases, in combination with active ingredients, such as antiinflammatory agents or antirheumatics, in order to antagonise their ulcerogenic potency and thus to reduce side effects. The compound (+)-4,9-dihydro-3-methyl-4-[(4-methyl-1-piperazinyl)-acetyl]-10H-thieno[3,4-b][1,5]benzodiazepin-10-one can furthermore be administered in combination with active ingredients for the treatment of diseases in which cholinergic mechanisms play an important role (such as, for example, asthma).

PHARMACOLOGY

The outstanding action of telenzepine can be demonstrated using the model of acetylcholine-induced bronchospasm in anaesthetised, spontaneously breathing guinea pigs (intravenous injection and intratracheally instillaton) and in conscious guinea pigs (oral administration):

Effect of Intravenously Administered Telenzepine on Acetylchline-Induced Bronchospasms in Anaesthetised, Spontaneously Breathing Guinea Pigs Experimental design Method for simultaneously recording pharmacodynamic or toxic effects on interior sensitive receptors and the respiration of guinea pigs (U. Kilian, E. Müller, E. Ch. Dittmann and J. Hamacher, Arzneim.-Forsch. 28, 1699–1708, 1978).

Guinea pigs

Pirbright White, Interfauna (Tuttlingen), 350–450 g, male.

Anaesthesia

Ethylurethane 1.2 g/kg i.p. as 12.5% aqueous solution.

Recording

Pneumotachogram: Maximum flow velocities of the respiratory air during expiration ($Vmax_e$, "peak flow"), tidal volume (TV).

Dosage

| | μmol/kg i.v., dissolved in 0.9% NaCl | | | | | | | |
|---|---|---|---|---|---|---|---|---|
| (±)-telenzepine | 0.03 | 0.05 | 0.1 | | 1 | 5 | | |
| (+)-telenzepine | 0.03 | 0.05 | 0.1 | 0.5 | 1 | | | |
| (−)-telenzepine | | | 0.1 | | 1 | 5 | 10 | 30 |

Acetylcholine as spasmogen, 0.2–0.3 μmol/kg i.v., dissolved in 0.9% NaCl.

Experimental procedure

−10 min control spasm, 0 min administration of substance, +2, +10, +20, +30, +60 min test spasms.

Evaluation

Determination of the effect of telenzepine on the parameters (mean and standard error of mean, n=10) and calculation of the bronchospasmolytic activity from this as percentage inhibition of the acetylcholine-induced decrease of $Vmax_e$ and TV by means of time-/effect curves. Computation of a dose/response curve of the mean bronchospasmolytic activity during the observation time (0–60 min) from the areas under the time/effect curves and reading of 1 h $ED_{50}$ values. Determination of a dose/response curve of the bronchospasmolytic activity at time 60 min and reading $ED_{50}$ values.

Results (±)-telenzepine and (+)-telenzepine exhibit dose-dependent and time-dependent inhibition of acetylcholine-induced bronchospasm in a very low dose range of 0.03–1 μmol/kg i.v. In spite of the i.v. route, the effect sets in slowly and reaches a plateau-like maximum between 30 and 10 min after administration, this maximum persisting over the observation period of 1 h. The onset of (−)-telenzepine efficacy is significantly delayed at doses between 0.1 and 1 μmol/kg i.v. and reaches a maximum between 10 and reaches a maximum between 10 and 30 μmol/kg i.v. The time/effect curve is comparable with those of both other forms of telenzepine.

Tables 1 and 2 describe the efficacy of telenzepine by means of dose/response curves of the mean activity for the entire observation period of 0–60 min and at time 60 min after administration. The $ED_{50}$ values derived therefrom are shown in Tables 3 and 4.

TABLE 1

Mean bronchospasmolytic activity of (±)-, (+)- and (−)-telenzepine during the entire observation period (0–60 min), expressed as the percentage increase of the maximum flow velocities of the respiratory air during expiration ($Vmax_e$) and of the tidal volume (TV) in acetylcholine-induced experimental spasm in comparison with the control spasm, $\bar{x} \pm SEM$, N=10.

| | μmol/kg i.v. | 0.03 | 0.05 | 0.1 | 0.5 | 1 | 5 | 10 | 30 |
|---|---|---|---|---|---|---|---|---|---|
| $Vmax_e$ | (±)-telenzepine | 7 ± 3 | 22 ± 3 | 61 ± 8 | | 81 ± 4 | 75 ± 3 | | |
| | (+)-telenzepine | 13 ± 4 | 21 ± 4 | 57 ± 5 | 87 ± 3 | 82 ± 3 | | | |
| | (−)-telenzepine | | | 2 ± 1 | | 17 ± 3 | 65 ± 4 | 79 ± 2 | 89 ± 3 |
| TV | (±)-telenzepine | 7 ± 3 | 26 ± 4 | 68 ± 9 | | 84 ± 4 | 86 ± 2 | | |
| | (+)-telenzepine | 17 ± 4 | 25 ± 5 | 62 ± 5 | 92 ± 3 | 85 ± 3 | | | |
| | (−)-telenzepine | | | 0 ± 2 | | 20 ± 5 | 74 ± 4 | 87 ± 2 | 98 ± 3 |

TABLE 2

Bronchospasmolytic activity of (±)-, (+)- and (−)-telenzepine at time 60 min after administration, expressed as the percentage increase of the maximum flow velocities of the respiratory air during expiration ($Vmax_e$) and of the tidal volume (TV) in acetylcholine-induced experimental spasm in comparison with the control spasm, x̄±SEM, N=10.

the recorded data, according to the method of Amdur and Mead (Amer. J. Physiol., 192, 364–368, 1958), before and at peak spasm, and determination of differences; calculation of percentage inhibition of the spasm after administration of the substance, in comparison with the control spasm; calculation of the dose/response curve and $ED_{50}$ values of this bronchospasmolytic activity.

| | μmol/kg i.v. | 0.03 | 0.05 | 0.1 | 0.5 | 1 | 5 | 10 | 30 |
|---|---|---|---|---|---|---|---|---|---|
| $Vmax_e$ | (±)-telenzepine | 11 ± 4 | 25 ± 3 | 70 ± 9 | | 82 ± 5 | 80 ± 4 | | |
| | (+)-telenzepine | 19 ± 6 | 35 ± 7 | 61 ± 6 | 95 ± 4 | 88 ± 4 | | | |
| | (−)-telenzepine | | | 1 ± 1 | | 18 ± 3 | 77 ± 5 | 77 ± 3 | 88 ± 4 |
| TV | (±)-telenzepine | 12 ± 6 | 32 ± 5 | 78 ± 11 | | 85 ± 5 | 91 ± 3 | | |
| | (+)-telenzepine | 23 ± 7 | 39 ± 7 | 64 ± 7 | 100 ± 4 | 88 ± 4 | | | |
| | (−)-telenzepine | | | −3 ± 3 | | 22 ± 5 | 88 ± 6 | 89 ± 3 | 94 ± 3 |

TABLE 3

$ED_{50}$ values of the mean bronchospasmolytic activity of (±)-, (+)- and (−)-telenzepine

| | $ED_{50}$ μmol/kg i.v. | | |
|---|---|---|---|
| | (±)-telenzepine | (+)-telenzepine | (−)-telenzepine |
| $Vmax_e$ | 0.08 | 0.1 | 3.1 |
| TV | 0.07 | 0.08 | 2.5 |

TABLE 4

$ED_{50}$ values of bronchospasmolytic activity of (±)-, (+)- and (−)-telenzepine at time 60 min after administration

| | $ED_{50}$ μmol/kg i.v. | | |
|---|---|---|---|
| | (±)-telenzepine | (+)-telenzepine | (−)-telenzepine |
| $Vmax_e$ | 0.08 | 0.07 | 3.2 |
| TV | 0.07 | 0.07 | 2.0 |

Effect of Intratracheally (i.t.) Administered (±)-Telenzepine on Acetylcholine-Induced Changes in Lung Function Parameters in Anaesthetised Guinea Pigs Experimental design Small-anmimal whole-body plethysmography in anaesthetised guinea pigs (method according to U. Heinreich and A. Wilhelm, in bga-Schriften 5/84, pp 255–266, MMW-Verlag, 1984).

Guinea pigs

Pirbright White, Interfauna (Tuttlingen). 290–350 g, male.

Anaesthesia

Ethylurethane 1.2 g/kg i.p. as 12.5% aqueous solution.

Recording

Plethysmographic measurement of maximum flow velocities of the respiratory air and tidal volume using tracheal catheter inserted through the natural passages; and measurement of intrapleural pressure using oesophageal catheter inserted through the natural passages.

Dosage 0.001, 0.01, 0.1 and 1 μmol/kg (±)-telenzepine i.t., dissolved in 0.1 ml/kg 0.9% NaCl+0.1% Tween 80, acetylcholine as spasmogen administered by inhalation of ultrasonically nebulized 0.18% acetylcholine/0.9% NaCl solution.

Experimental procedure

−10 min control spasm, 0 min administration of substance, +5 and +30 min test spasms.

Evaluation

Computation of conductance (=capacity of airways to conduct air, equivalent to reciprocal of airway resistance) and of compliance (=distensibility of lung) from Results (±)-telenzepine exhibits time-dependent and dose-dependent inhibition of acetylcholine-induced reduction of conductance and compliance in the broad but extremely low dose range of 0.001–1 μmol/kg i.t.; the efficacy is more pronounced at 30 min than at 5 min after administration.

Table 5 describes the efficacy of (±)-telenzepine 5 and 30 min after administration by means of dose/response curves. The $ED_{50}$ values derived therefrom are shown in Table 6.

TABLE 5

Bronchospasmolytic activity of (±)-telenzepine 5 and 30 min after administration, expressed as the percentage increase of conductance and compliance in acetylcholine-induced experimental spasm in comparison with the control, x̄±SEM, N=10.

| μmol/kg i.t. | | 0.001 | 0.01 | 0.1 | 1 |
|---|---|---|---|---|---|
| 5 min | Conductance | 12 ± 3 | 62 ± 10 | 46 ± 10 | 65 ± 9 |
| | Compliance | 5 ± 1 | 50 ± 9 | 34 ± 10 | 57 ± 9 |
| 30 min | Conductance | 20 ± 5 | 51 ± 9 | 54 ± 7 | 84 ± 2 |
| | Compliance | 13 ± 3 | 49 ± 9 | 51 ± 9 | 89 ± 4 |

TABLE 6

$ED_{50}$ values of bronchospasmolytic activity of (±)-telenzepine after i.t. instillation.

| | $ED_{50}$ (μmol/kg i.t.) | |
|---|---|---|
| | 5 min p.a. | 30 min p.a. |
| Conductance | 0.05 | 0.03 |
| Compliance | 0.3 | 0.03 |

Effect of orally administered (±)-telenzepine on acetylcholine-induced asthma attacks in the conscious guinea pig Experimental design As described by R. Beume, U. Kilian, N. Kolassa, K. Mussler, Atemw.-Lungenkrkh., 11, 342–345, 1985 ("The testing of bronchospasmolytic substances in conscious guinea pigs").

Guinea pigs

Pirbright White, Interfauna (Tuttlingen), 250–450 g, male, 10 animals per dose and experiment.

Recording and evaluation

Thoracographic measurement of the respiratory activity, measurement of the latency period from the beginning of acetylcholine nebulisation to the beginning of the asthma attack; determination of the number of animals for which, 30 minutes after administration, the latency period of the experimental attack has been at least tripled in relation to the control attack; estimation of the approximate $ED_{50}$ from this.

Dosage 0.1, 0.3, 1, 3, 10 and 30 μmol/kg (±)-telenzepine p.o. (in 4% Methocel, administered in 0.9% NaCl); acetylcholine 0.09% in 0.9% NaCl by inhalatin (ultrasonic nebulisation).

Results

The number of animals for which there is at least a tripling of the latency period of the acetylcholine-induced experimental attack in comparison with the control attack as a function of the perorally administered (±)-telenzepine dose is expressed as follows:

|           | Number of animals | |
|-----------|------|------------------------|
| μmol/kg p.o. | Used | Latency period tripled (= protected) |
| 0.1 | 10 | 3 |
| 0.3 | 10 | 5 |
| 1 | 10 | 6 |
| 3 | 10 | 7 |
| 10 | 10 | 9 |
| 30 | 10 | 10 |

This gives an approximate $ED_{50}$ of 0.7 (0.3–1.7 95% Int.) μmol/kg p.o.

RECEPTOR AFFINITY STUDIES

The affinity of (±)-4,9-dihydro-3-methyl-4-[(4-methyl-1-piperazinyl)-acetyl]-10H-thieno[3,4-b][1,5]benzodiazepin-10-one (telenzepine, compound 2 in Table 7) and its conformers [(+)-enantiomer=compound 1, (−)-enantiomer=compound 3] to muscarinic $M_1$ (ganglionic type) and $M_2$ (cardiac type) receptors was investigated by the following methods:

Method 1

Electrically Stimulated Rabbit vas Deferens in Organ Bath (Eltze, M., 1988, Submitted for Publication in Europ. J. Pharmacol.)

Isometric contractions (HSE force transducer, K-30; tilt and zones, BD-9 chart recorder) of isolated seminal duct sections of rabbits (male, white New Zealand rabbits, 2.5–3.5 kg) were recorded in an organ bath (10 ml, 31° C., gassing with carbogen, initial tension of the organs 0.75 g) under electrical stimultion (HSE stimulator; hook-shaped Pt electrode 1 cm below the water surface of the bath; 30 V, 0.5 ms, 0.05 Hz). After an equilibration time of 30 minutes, cumulative dose/response curves of McN-A-343 ($10^{-7}-2 \times 10^{-6}$M) were recorded simultaneously on 8 organ sections in each case (control curves), using the technique described by van Rossum (1963). After 3 control curves, a fixed concentration of the agonist (for example $5 \times 10^{-7}$, $10^{-6}$, $3 \times 10^{-6}$, $10^{-5}$ or $3 \times 10^{-5}$M) per organ section was applied and, after stabilisation of the effect, increasing concentrations of the agonist to be tested were added. The nutrient solution used had the following composition (mM): NaCl 118, KCl 4.7, $CaCl_2 \cdot 2H_2O$ 2.5, $MgSO_4 \cdot 7H_2O$ 0.6, $KH_2PO_4$ 1.2, $NaHCO_3$ 25.0 and glucose 11.1. In order to block $\alpha_2$-adrenoreceptors, the nutrient solution additionally contained $10^{-6}$M yohimbine.

Method 2

Electrically Stimulated Left Atrium of the Rat (Eltze et al., 1985, Europ. J. Pharmacol. 112, 211-224).

Isometric contractions (HSE force transducer, K-30; Watanabe Linear Corder Mark 5) of isolated, left atria of rats (male 250–350 g) were recorded in an organ bath (10 ml, Tyrode nutrient solution, 31° C., gassing with carbogen, initial tension of the organs 0.25 g) under electrical stimulation (HSE stimulator; hook-shaped Pt electrodes at the base of the bath and immersed, annular Pt electrodes 1 cm below the water surface of the bath; 7 V, 3 ms, 2 Hz). After an equilibration time of 30 minutes, cumulative dose/response curves of carbachol ($10^{-8}-10^{-6}$M, in the presence of the antagonist also up to $10^{-5}$ or $10^{-4}$M) were recorded simultaneously on 4 organs in each case by the technique described by van Rossum (1963). The substance to be tested was added to the organ baths 20 minutes before application of the carbachol. The pauses between the individual dose/response curves were 30–45 minutes.

The Tyrode nutrient solution used had the following composition (mM): NaCl 130, KCl 2.0, $CaCl_2 \cdot 2H_2O$ 1.8, $MgCl_2 \cdot 6H_2O$ 0.98, $NaHCO_3$ 12.0, $NaH_2PO_4$ 0.42 and glucose monohydrate 5.6. $pA_2$ values (−log of the molar dissociation constants of the competitive antagonist-receptor complex) were determined by linear regression using the Schild plot: $pA_2 = -\log[B/(x-1)]$, (Arunlakshana and Schild, 1959).

Table 7 below gives $pA_2$ values of the substances, for which the slope of the regression lines for theoretically competitive antagonism have been normalised to 1.00 (Tallarida et al., 1979).

TABLE 7

Affinity of (±)-4,9-dihydro-3-methyl-4-[(4-methyl-1-piperazinyl)-acetyl]-10H-thieno[3,4-b][1,5]benzodiazepin-10-one (telenzepine=compound 2) and its conformers [(+)-enantiomer=compound 1, (−)-enantiomer=compound 3] to $M_1$ and $M_2$ receptors

| Substance | $M_1$ receptor (ganglionic) was deferens of the rabbit | | $M_2$ receptor (cardiac) left atrium of the rat | |
|---|---|---|---|---|
|  | $pA_2 \pm$ SEM | n | $pA_2 \pm$ SEM | n |
| Compound 1 | 9.12 ± 0.08 | 7–18 | 7.67 ± 0.08 | 15–20 |
| Compound 2 | 8.86 ± 0.06 | 20 | 7.32 ± 0.09 | 6–11 |
| Compound 3 | 6.98 ± 0.14 | 11–18 | 6.12 ± 0.06 | 11–15 |

Ref

Van Rossum J. M., 1963, Arch. int. Pharmacodyn. 143, 299.

Eltze, M. et al., 1985, Europ. J. Pharmacol. 112, 211.

Arunlakshana O. and H. O. Schild, 1959, Br. J. Pharmacol. 14, 48.

Tallarida R. J. et al., 1979, Life Sci. 25, 637.

Eltze M., 1988, Submitted for publication in Europ. J. Pharmacol.

Testing the Antiulcerogenic and Secretion-Inhibiting Action on the Modified Shay Rat The excellent gastric protective action and the gastric secretion-inhibiting action of the compound (+)-4,9-dihydro-3-methyl-4-[(4-methyl-1-piperazinyl)-acetyl]-10H-thieno[3,4-b][1,5]benzodiazepin-10-one (=compound 1 in Table 8 below) in comparison with the corresponding (−)-enantiomer (=compound 3) and with the racemate (=compound 2) can be detected in studies on the modified Shay rat. The effect of the stated compounds after intravenous (i.v.) administration on the formation of lesions and the acid secretion in the modified Shay rat is shown in Table 8 below.

TABLE 8

| Serial No. | N (Number of animals) | Gastric protective action Reduction of lesion index, about ED50+) (mg/kg) i.v. | Inhibition of acid secretion Reduction of HCl secretion, about ED50+) (mg/kg) i.v. |
|---|---|---|---|
| 1 | 24 | 0.01 | 0.085 |
| 2 | 24 | 0.042 | 0.18 |
| 3 | 24 | 0.65 | 3.0* |

+) ED50 = Dose (interpolated), which reduces the lesion index or the HCl secretion of the rat stomach in the treated group by 50% compared with the control group.
*Inhibition following 3 mg: 46%

METHOD

Ulcers are provoked in rats (female, 180–200 g, 4 animals per cage on high grids) which have fasted for 24 hours, by pylorus ligature (under diethyl ether anaesthesia) and oral administration of 100 mg/10 ml/kg of acetylsalicylic acid. The substances to be tested are administered intravenously (1 ml/kg) directly after the pylorus ligature. The wound is closed by means of Michel clamps. 4 hours afterwards, the animals are sacrificed under anaesthesia with ether by Atlas dislocation, and resection of the stomach.

The stomach is opened along the greater curvature and clamped to a cork sheet, the amount of secreted gastric juice (volume) is determined first and its HCl content (titration with sodium hydroxide solution) being determined subsequently. The number and size (=diameter) of ulcers present are determined using a stereomicroscope, under 10×magnification. The product of severity (according to the following point scale) and number of ulcers serves as an individual lesion index.

| Point scale: | | |
|---|---|---|
| No ulcers | | 0 |
| Ulcer diameter | 0.1–1.4 mm | 1 |
| | 1.5–2.4 mm | 2 |
| | 2.5–3.4 mm | 3 |
| | 3.5–4.4 mm | 4 |
| | 4.5–5.4 mm | 5 |
| | >5.5 mm | 6 |

The reduction in the means lesion index of each treated group compared with the control group (=100%) serves as a measure of the antiulcerogenic effect. The ED50 is the dose which reduces the mean lesion index or the HCl secretion by 50% compared with the control.

We claim:

1. A process for the preparation of the (+)- and (−)-conformer of the 4,9-dihydro-3-methyl-4-[(4-methyl-1-piperazinyl)-acetyl]-10H-thieno-[3,4-b][1,5]benzodiazepin-10-one (=compound of the formula I), characterised in that the conformer mixture of the compound of the formula I is reacted with a chiral compound which has a uniform configuration and is of the formula II, wherein R represents a chiral radical having a uniform configuration and wherein R represents $R_1$—O—$CH_2$— where $R_1$ together with the oxygen atom to which it is bonded represents a glycosyl radical, a chiral terpene alcohol radical or another chiral alcohol radical and X represents a leaving group selected from halogen, —O—$SO_2$—$CH_3$, —$OSO_2CF_3$ or —O—$SO_2$—$C_6H_4$—p—$CH_3$, the resulting diastereomer mixture III is separated and the compounds I having a uniform conformation are liberated from the optically pure diastereomers.

2. A process according to claim 1, characterized in that R represents an isopinocampheyloxymethyl radical.

3. The compound: (+)-4,9-dihydro-3-methyl-4-[(4-methyl-1-piperazinyl)-acetyl]-10H-thieno-[3,4-b][1,5]benzodiazepin-10-one or a pharmaceutically-acceptable salt thereof.

4. A method for treatment or prophylaxis of a bronchial disease in a mammal afflicted with or subject to attacks of such disease, which method comprises administering to the mammal an effective amount of 4,9-dihydro-3-methyl-4-[(4-methyl-1-piperazinyl)-acetyl]-10H-thieno[3,4-b][1,5]benzodiazepin-10-one or of a pharmacologically-tolerated salt thereof.

5. A method of claim 4 wherein the dihydrothienobenzodiazepinone is (+)-4,9-dihydro-3-methyl-4-[(4-methyl-1-piperazinyl)-acetyl]-10H-thieno[3,4-b][1,5]-benzodiazepin-10-one or a pharmacologically-tolerated salt thereof.

6. A compound which is 4,9-dihydro-3-methyl-4-[(4-methyl-1-piperazynyl)-acetyl]-9-R-10H-thieno[3,4-b][1,5]benzodiazepin-10-one, wherein R is a chiral radical having a uniform configuration, or a salt thereof.

7. A compound of claim 6 wherein R is an isopinocampheyloxymethyl radical, or a salt thereof.

8. A pharmaceutical composition, useful for treatment or prophylaxis of a bronchial disease in a mammal, comprising an effective amount of the compound of claim 3 or of a pharmacologically-tolerated salt thereof and a pharmacologically-acceptable carrier.

9. The compound of claim 3 substantially free from its enantiomer, or a pharmacologically-acceptable salt thereof.

* * * * *